(12) United States Patent
Pham et al.

(10) Patent No.: US 9,566,673 B2
(45) Date of Patent: Feb. 14, 2017

(54) SNARE INTRODUCER

(71) Applicant: Merit Medical Systems, Inc., South Jordan, UT (US)

(72) Inventors: Vinny K. Pham, Salt Lake City, UT (US); Eric Stenzel, Galway County (IE); Paul Byrne, Tuam (IE); Mark Flygare, Farmington, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 337 days.

(21) Appl. No.: 13/759,725

(22) Filed: Feb. 5, 2013

(65) Prior Publication Data

US 2013/0205584 A1    Aug. 15, 2013

Related U.S. Application Data

(60) Provisional application No. 61/597,472, filed on Feb. 10, 2012.

(51) Int. Cl.
| | |
|---|---|
| *A61B 17/3205* | (2006.01) |
| *B23P 19/00* | (2006.01) |
| *A61M 25/06* | (2006.01) |
| *A61M 25/00* | (2006.01) |
| *A61B 17/00* | (2006.01) |

(52) U.S. Cl.
CPC .......... *B23P 19/00* (2013.01); *A61B 17/32056* (2013.01); *A61M 25/0662* (2013.01); *A61B 2017/0053* (2013.01); *A61B 2017/00526* (2013.01); *A61M 25/0097* (2013.01); *Y10T 29/53126* (2015.01)

(58) Field of Classification Search
CPC ............ A61B 17/32056; A61B 17/221; A61B 2017/2212; A61B 2017/00358; A61M 25/0662; A61M 25/0668; A61M 2025/0681; A61M 2025/0188; A61M 25/09041

See application file for complete search history.

(56) References Cited

U.S. PATENT DOCUMENTS

| | | |
|---|---|---|
| 5,273,042 A | 12/1993 | Lynch |
| 5,282,479 A | 2/1994 | Havran |
| 6,053,934 A * | 4/2000 | Andrews et al. .............. 606/207 |
| 7,682,365 B2 * | 3/2010 | Guinan ......................... 606/108 |
| 7,708,744 B2 | 5/2010 | Soma et al. |
| 2002/0111585 A1 * | 8/2002 | Lafontaine ............... 604/167.06 |

(Continued)

FOREIGN PATENT DOCUMENTS

| | | |
|---|---|---|
| WO | WO 2005/072402 | 8/2005 |
| WO | WO 2011/075727 | 6/2011 |

OTHER PUBLICATIONS

International Search Report and Written Opinion dated May 15, 2013 for PCT/US2013/024767.

(Continued)

*Primary Examiner* — Imani Hayman
*Assistant Examiner* — James D Ponton
(74) *Attorney, Agent, or Firm* — Stoel Rives LLP

(57) ABSTRACT

An introducer with a longitudinal slit is disclosed. The slit may enable a practitioner to remove the introducer from an elongate instrument without removing the elongate instrument from a hub or catheter. A hub having a hub taper is also disclosed. The hub taper may be configured to retain the introducer within the hub in some embodiments.

12 Claims, 12 Drawing Sheets

(56) References Cited

U.S. PATENT DOCUMENTS

| | | |
|---|---|---|
| 2003/0073955 A1 | 4/2003 | Otawara |
| 2004/0059371 A1 | 3/2004 | Healy et al. |
| 2005/0085746 A1* | 4/2005 | Adams .............. A61M 25/0662 600/585 |
| 2005/0234505 A1 | 10/2005 | Diaz et al. |
| 2009/0131749 A1* | 5/2009 | Ahmed et al. ................ 600/106 |
| 2010/0217208 A1 | 8/2010 | Snow |
| 2010/0268123 A1* | 10/2010 | Callahan ........... A61M 25/0668 600/588 |

OTHER PUBLICATIONS

Extended European Search Report dated Mar. 31, 2015 for EP13746173.7.

* cited by examiner

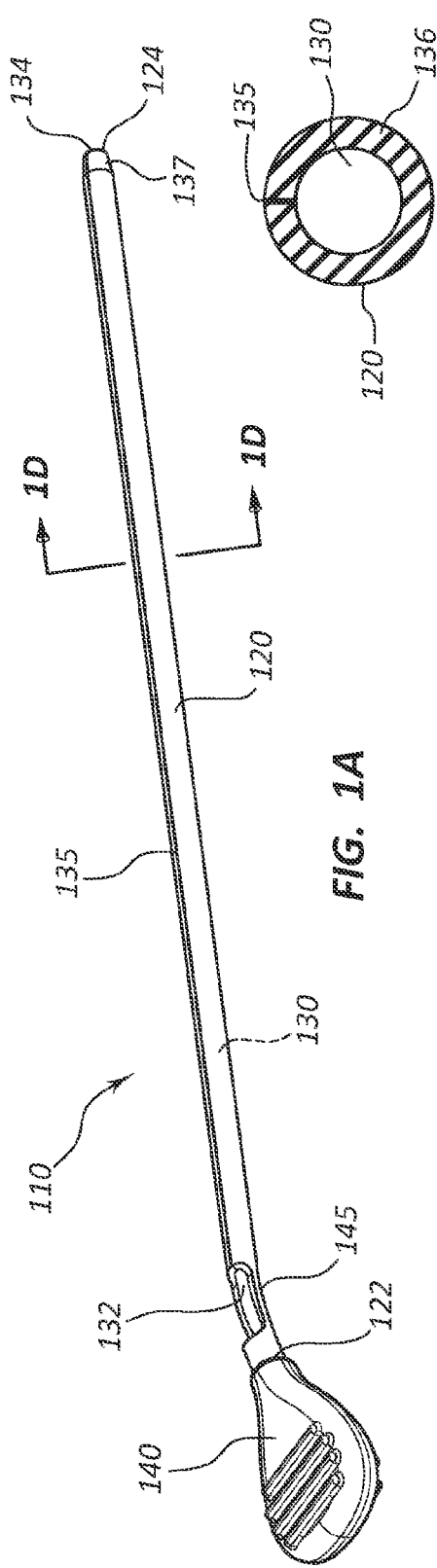
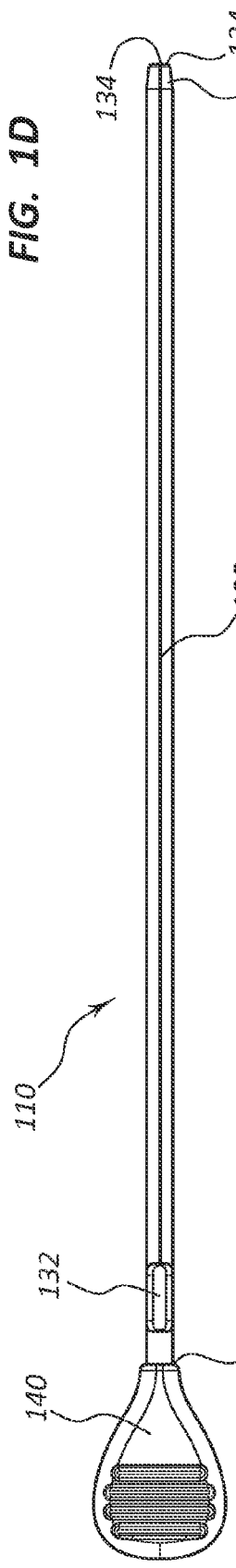
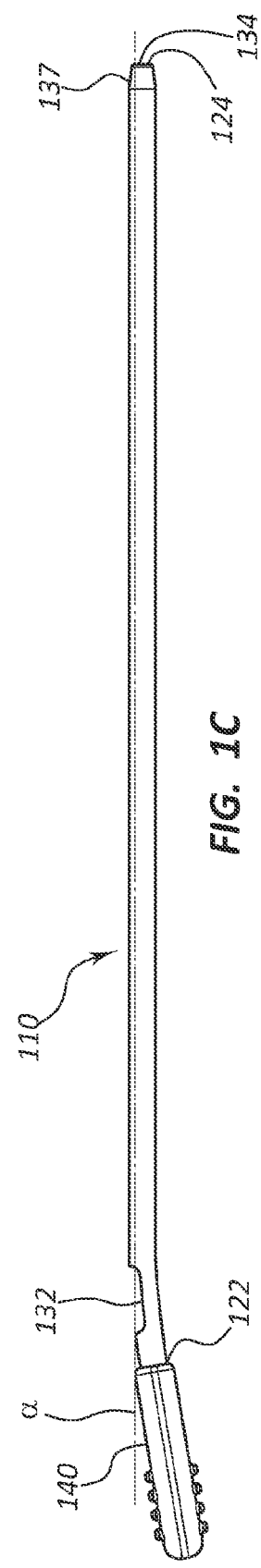
FIG. 1A
FIG. 1B
FIG. 1C
FIG. 1D

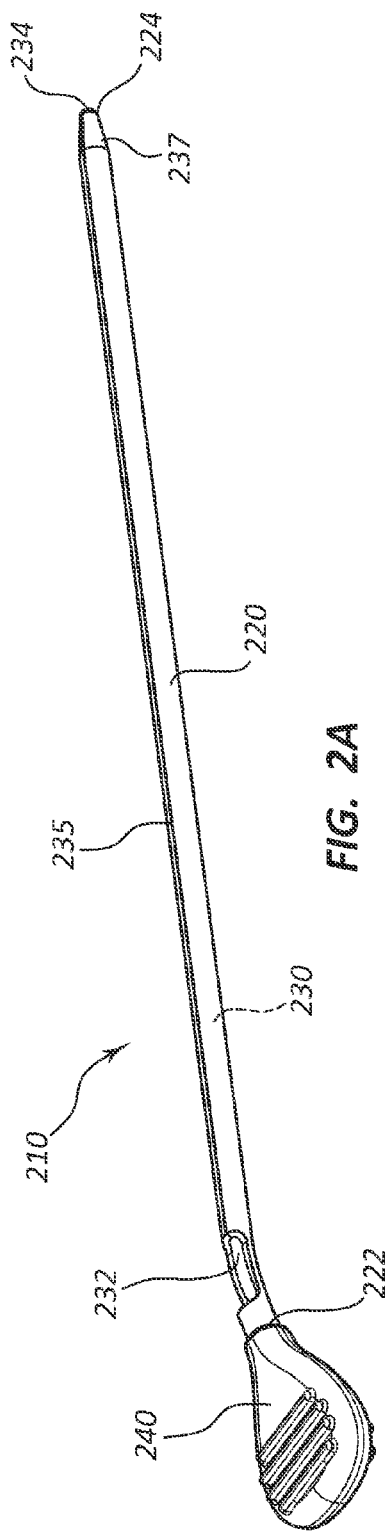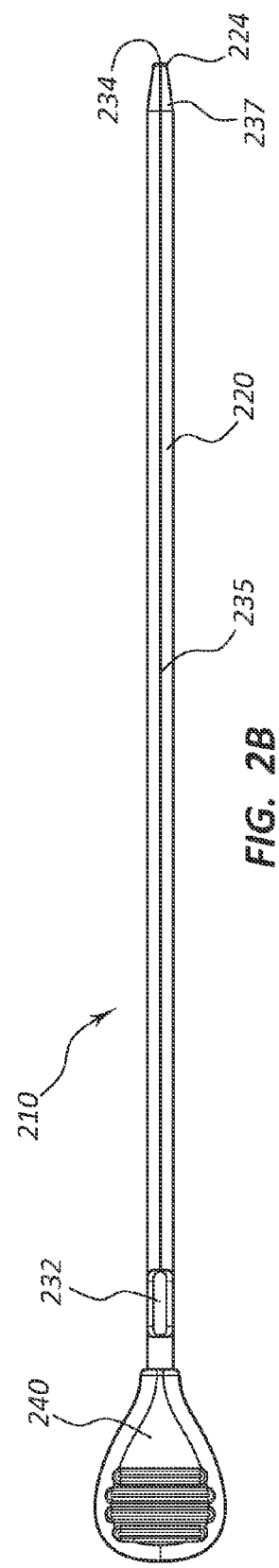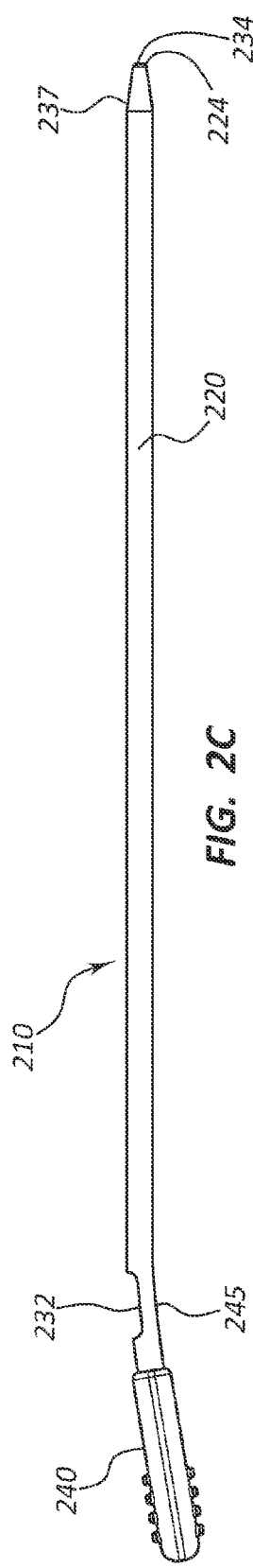

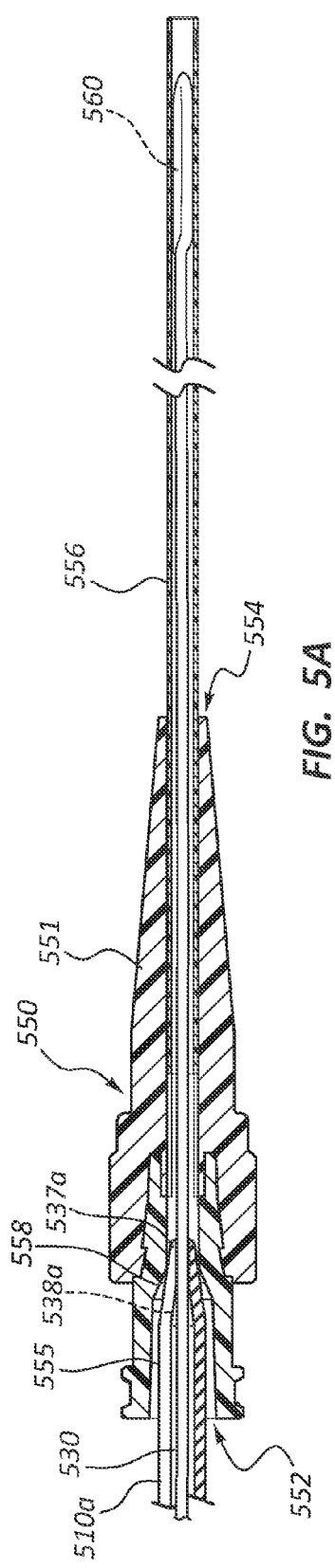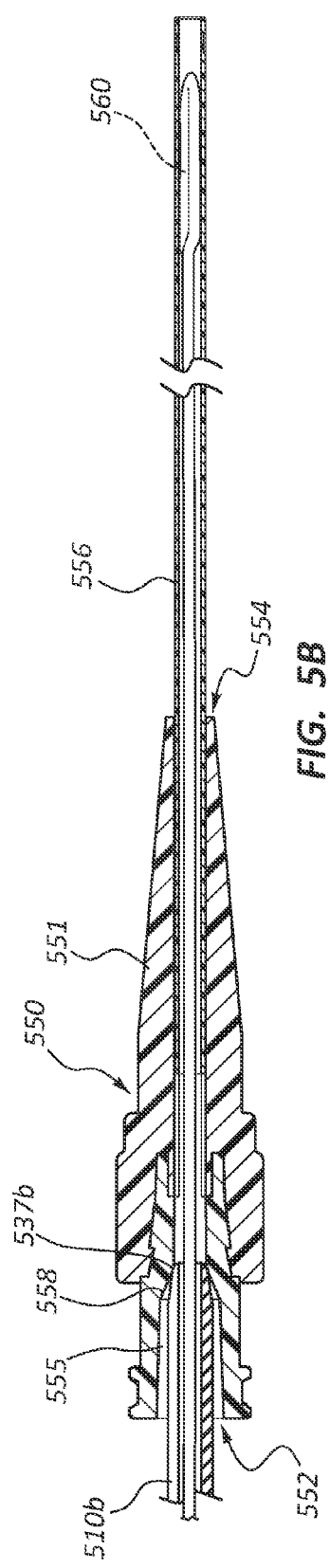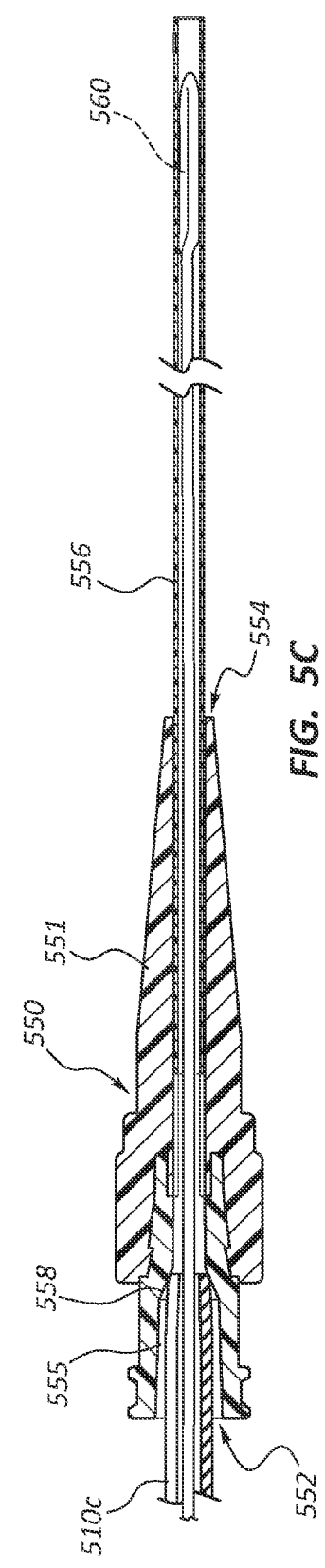

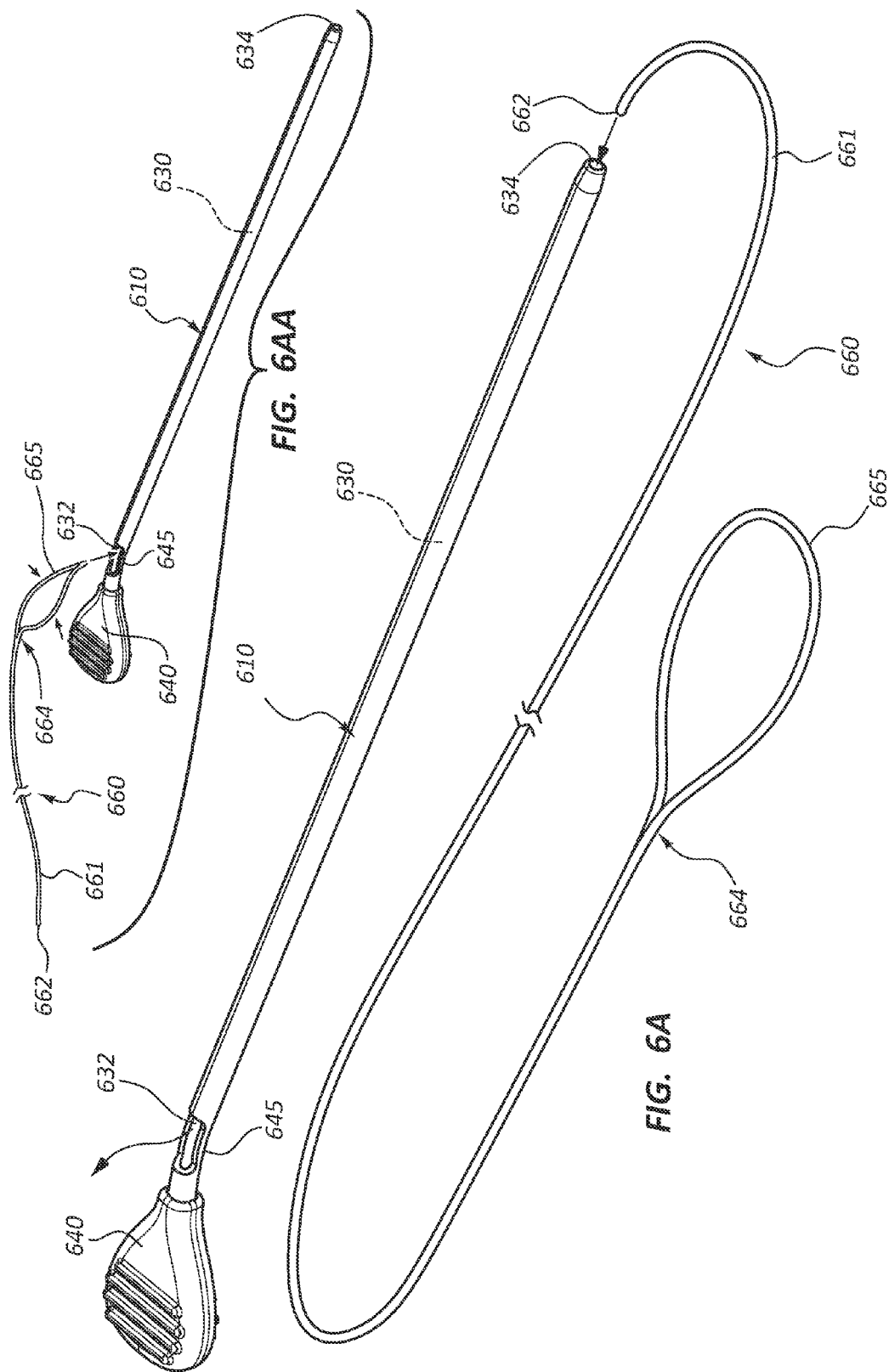

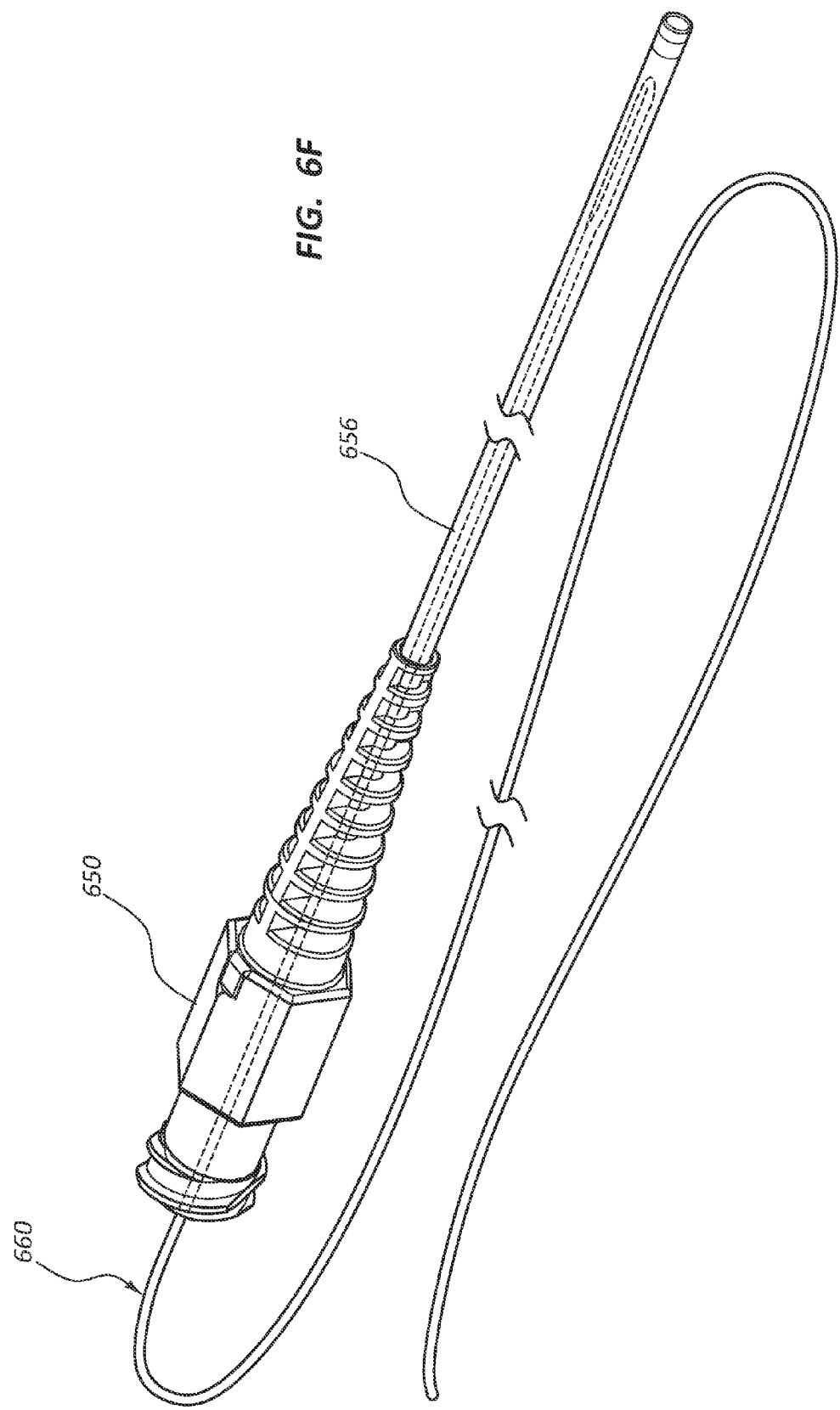

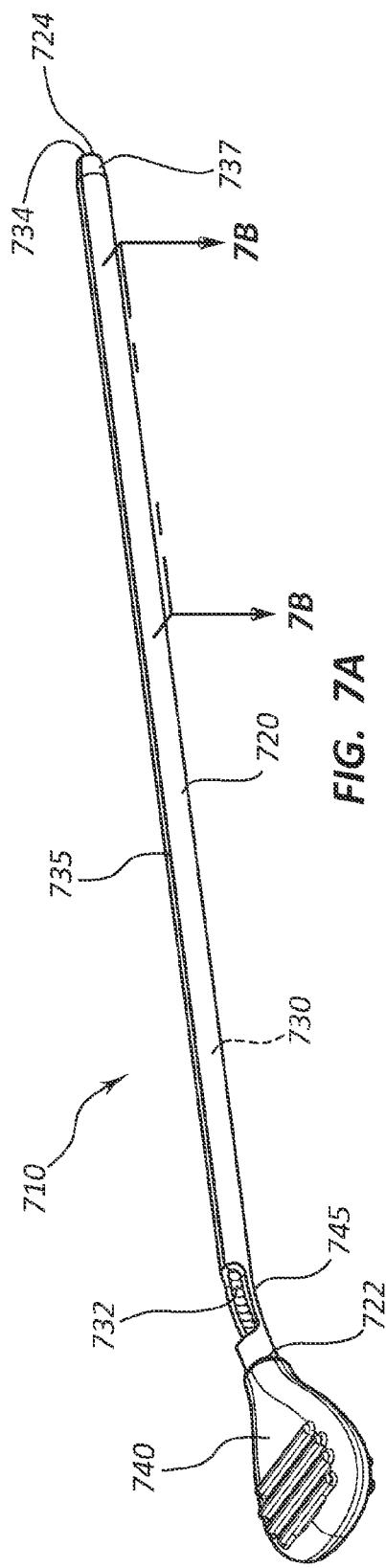
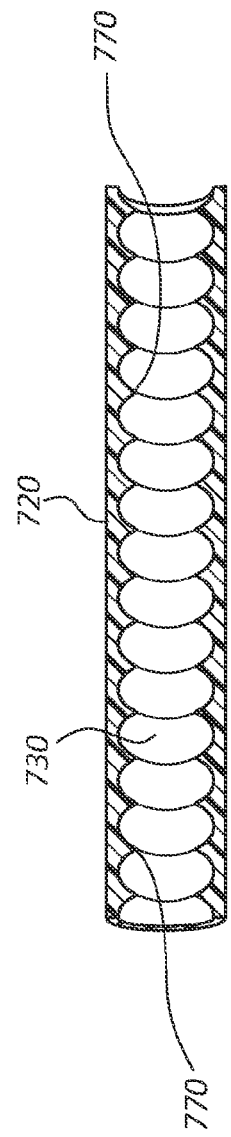
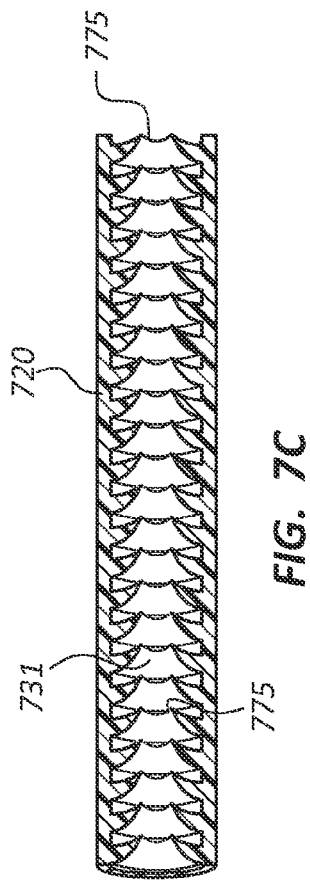
FIG. 7A
FIG. 7B
FIG. 7C ial Patent Application No. 61/597,472, filed Feb. 10, 2012, which is herein incorporated by reference in its entirety.

SNARE INTRODUCER

RELATED APPLICATIONS

This application claims priority to U.S. Provisional Patent Application No. 61/597,472, filed Feb. 10, 2012, which is herein incorporated by reference in its entirety.

TECHNICAL FIELD

The present disclosure relates generally to devices configured to aid in the introduction of elongate instruments into lumens. For example, in some embodiments the present disclosure relates to devices configured to aid in the introduction of a snare into a catheter.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a perspective view of one embodiment of an introducer.

FIG. 1B is a top view of the introducer of FIG. 1A.

FIG. 1C is a side view of the introducer FIGS. 1A and 1B.

FIG. 1D is a cross sectional view of the introducer of FIG. 1A, taken through line 1D-1D as indicated in FIG. 1A.

FIG. 2A is a perspective view of another embodiment of an introducer.

FIG. 2B is a top view of the introducer of FIG. 2A.

FIG. 2C is a side view of the introducer of FIGS. 2A and 2B.

FIG. 5A is a cross sectional view of an introducer within a hub with a snare.

FIG. 5B is a cross sectional view of another embodiment of an introducer within a hub with a snare.

FIG. 5C is a cross sectional view of yet another embodiment of an introducer within a hub.

FIG. 6A is a perspective view of an introducer and a snare.

FIG. 6AA is a perspective view of the introducer and snare of FIG. 6A in another configuration.

FIG. 6F is a perspective view of the snare, hub, and catheter of FIG. 6E with the introducer removed.

FIG. 7A is a perspective view of another embodiment of an introducer.

FIG. 7B is a cross sectional view of the introducer of FIG. 7A taken through plane 7B-7B.

FIG. 7C is a cross sectional view of an alternate embodiment of an introducer.

DETAILED DESCRIPTION

Figure 3A:
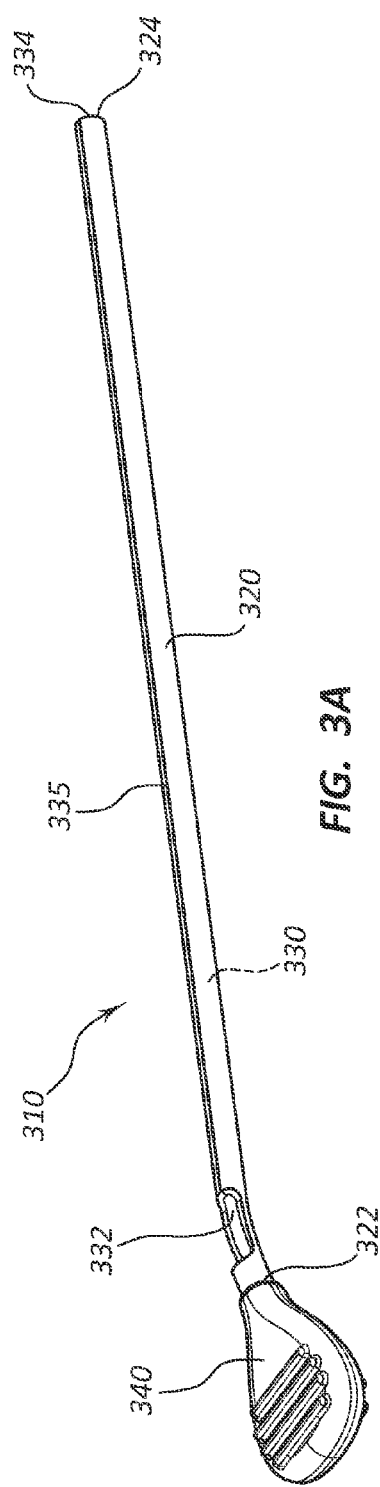
FIG. 3A is a perspective view of another embodiment of an introducer.

An introducer may be configured to aid in disposing an elongate instrument into a lumen. In some embodiments, an introducer may radially compress a portion of an instrument, such as a snare loop, for introduction into a lumen such as a catheter lumen.

Though many of the examples provided herein may refer specifically to the introduction of snare loops into catheter lumens, the current disclosure is applicable to any instrument, component, element, or part to be introduced into a confined space, such as a lumen. For example, forceps, snares with multiple loops, guidewires, and other tools may be disposed first within an introducer, then advanced or otherwise transferred to another confined space, such as a lumen.

It will be readily understood with the aid of the present disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner during use, while the distal end is the opposite end. For example, the proximal end of an elongate instrument or tool refers to the end nearest the practitioner when the instrument is in use. In some instances the distal end of such tools may be configured to be disposed within the body of a patient.

FIG. 1A is a perspective view of one embodiment of an introducer 110. In the illustrated embodiment, the introducer 110 comprises an elongate body member 120 having a proximal end 122 and a distal end 124. The body member 120 may further be understood as having a longitudinal axis running between the proximal 122 and distal 124 ends of the body member 120. This longitudinal axis is not a component of the system, but rather refers to an imaginary line along the length of the body member 120. In embodiments where the body member 120 is not substantially straight, the longitudinal axis of the body member 120 would also not be straight, following the contours of the body member 120 between the proximal 122 and distal 124 ends of the body member 120.

FIG. 1B is a top view of the introducer 110 of FIG. 1A, while FIG. 1C is a side view of the introducer 110 of FIG. 1A. FIG. 1D is a cross sectional view of the introducer of FIG. 1A, taken through line 1D-1D as indicated in FIG. 1A.

The introducer 110 of FIGS. 1A-1D further comprises a lumen 130 disposed within the body member 120. In some embodiments the lumen 130 may be radially centered within the body member 120. Thus, in such embodiments, the body member 120 together with the lumen 130 may be understood to define a substantially tubular shape. The body member 120 and lumen 130 need not have circular or substantially circular cross sectional profiles. It is within the scope of this disclosure for one or both of these elements to have any cross sectional profile, such as elliptical or polygonal.

The introducer 110 may further include a distal opening 134 extending between the lumen 130 and the exterior of the body member 120. In some embodiments the distal opening 134 may be located at the distal end 124 of the body member 120. In other embodiments, the distal opening 134 may be adjacent the distal end 124 of the body member 120, though not necessarily located precisely at the distal end 124 of the body member 120.

The introducer 110 may also be provided with a side port 132 positioned adjacent the proximal end 122 of the body member 120. In the illustrated embodiment, the side port 132 extends from the lumen 130 to the exterior of the body member 120, the side port 132 extending through the sidewall 136 of the body member 120. In another embodiment the side port 132 may be replaced by (or used on combination with) a proximal opening (not shown) located at or adjacent the proximal end 122 of the body member 120, though not necessarily extending through a sidewall 136 of the body member 120. In some instances the side port 132 comprises an elongate hole in the side of the body member 120.

As further detailed below in connection with, for example, FIG. 6A, the distal opening 134 and side port 132 may be utilized to allow an elongate instrument to be disposed within the lumen 130 of the body member 120, with the proximal and distal ends of the elongate instrument extending from the side port 132 and distal opening 134 in some instances.

In some embodiments, the introducer 110 may further comprise a slit 135 in a sidewall 136 of the body member 120. In the exemplary embodiment, the slit 135 extends along the longitudinal axis of the body member 120 between the side port 132 and the distal opening 134. The side port 132 has a first width and the slit 135 has a second width. In the exemplary embodiment, the second width is smaller than the first width.

The embodiment illustrated in FIGS. 1A-1D further comprises a tab 140 coupled to the proximal end 122 of the body member 120. The tab 140 may be configured to be graspable by a user, providing a handle or location where a user may grasp the introducer 110 when the device is in use. In some instances, the tab 140 may be configured to provide a handle which is located proximal of the side port 132, which may allow a user to grasp the introducer 110 without compressing the side port 132 or the slit 135. In some embodiments, an introducer 110 may be configured such that a portion of the body member 120 is directly graspable by a user, in place of, or in connection with a tab 140. For example, the proximal end 122 of the body member 120 may simply extend beyond the side port 132 in some instances, allowing a user to grasp the body member 120 proximal of the side port 132.

Furthermore, in the illustrated embodiment the body member 120 is configured with a bend 145. In the illustrated embodiment, the bend 145 is located at substantially the same position along the longitudinal axis of the body member 120 as the side port 132. Again, as further detailed below, a bend 145 so positioned may facilitate the threading of an elongate instrument through the lumen 130 from the distal opening 134 to the side port 132. In some embodiments the bend 145 may be configured such that there is a straight line, or line of sight, from the exterior of the body member 120 through the distal opening 134 and lumen 130 and out of the side port 132. This line is illustrated by line α(alpha) in FIG. 1C.

The introducer 110 may also comprise an outside taper 137 which may be positioned at or adjacent the distal end 124 of the body member 120. In some embodiments, such as the embodiment of FIGS. 1A-1C, the outside taper 137 may define a tapered portion, wherein the outside diameter of the body member 120 decreases along a portion of the body member in the longitudinal direction from the proximal end of the tapered portion to the distal end of the tapered portion.

FIGS. 2A-2C are views of another embodiment of an introducer that can, in certain respects, resemble components of the introducer described in connection with FIGS. 1A-1D above. It will be appreciated that all the illustrated embodiments may have analogous features. Accordingly, like features are designated with like reference numerals, with the leading digits incremented to "2." (For instance, the introducer is designated "110" in FIG. 1A, and an analogous introducer is designated as "210" in FIG. 2A.) Relevant disclosure set forth above regarding similarly identified features thus may not be repeated hereafter. Moreover, specific features of the introducer and related components shown in FIGS. 2A-2C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the introducer of FIG. 2A-2C. Any suitable combination of the features, and variations of the same, described with respect to the introducer and components illustrated in FIGS. 1A-1D, can be employed with the introducer and components of FIGS. 2A-2C, and vice versa. This pattern of disclosure applies equally to further embodiments depicted in subsequent figures and described hereafter.

FIG. 2A is a perspective view of the second illustrated embodiment of an introducer 210 while FIG. 2B is a top view of the introducer 210 of FIG. 2A and FIG. 2C is a side view of the introducer 210 of these figures.

The introducer 210 of FIGS. 2A-2C comprises a body member 220 which defines a proximal end 222 and a distal end 224 with a longitudinal axis running between these ends. The introducer 210 further comprises a lumen 230 with a distal opening 234 and a side port 232. The lumen 230 is further provided in communication with a slit 235 extending between the side port 232 and the distal opening 234.

As compared to the embodiment of FIGS. 1A-1D, the introducer 210 of FIGS. 2A-2C comprises an outside taper 237 which is relatively longer in the longitudinal direction, and which tapers to a relatively smaller minimum outside diameter than the outside taper 137 of FIGS. 1A-1D. Additionally, in some instances, the angle formed between the outside surface of the taper 237 and the outside surface of the non tapered portion of the introducer 210 may be greater in some embodiments, relative to other embodiments. In some instances an introducer, such as introducer 210 of FIGS. 2A-2C may be configured with a taper 237 which tapers to a relatively smaller outside diameter in order to facilitate use of the introducer with relatively smaller hubs and catheters or with relatively small elongate instruments (as further outlined below in connection with FIG. 6A, for example). Moreover, in some embodiments, an introducer may have multiple tapered portions and/or stepped portions along the outside diameter. Introducers with multiple tapers or steps may have a relatively large reduction in outside diameter from the body of the introducer to the tapered end.

Figure 3B:
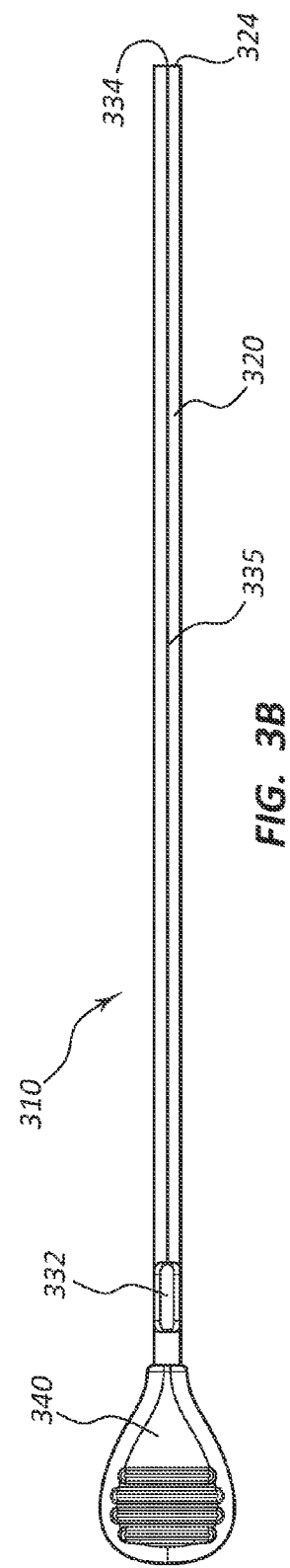
FIG. 3B is a top view of the introducer of FIG. 3A.
Figure 3C:
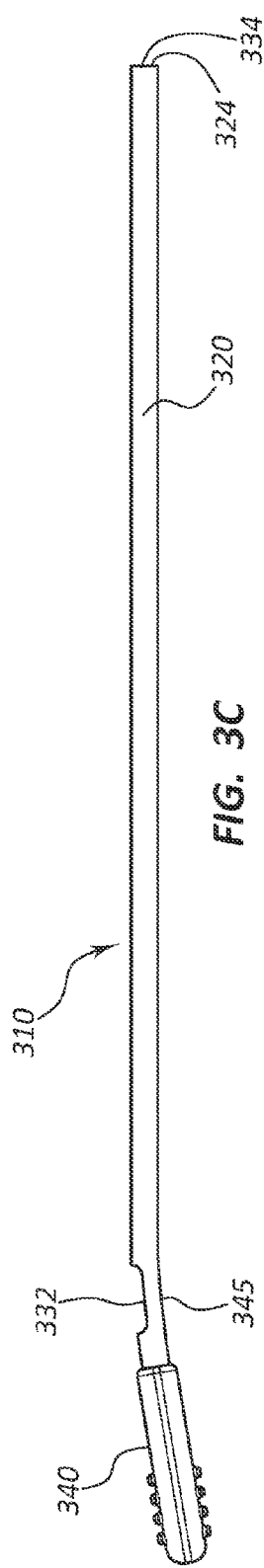
FIG. 3C is a side view of the introducer of FIGS. 3A and 3B.

FIG. 3A is a perspective view of another embodiment of an introducer 310 while FIG. 3B is a top view of the introducer 310 of FIG. 3A and FIG. 3C is a side view of the introducer 310 of these figures.

The introducer 310 of FIGS. 3A-3C comprises a body member 320 which defines a proximal end 322 and a distal end 324 with a longitudinal axis running between these ends. The introducer 310 further comprises a lumen 330 with a distal opening 334 and a side port 332. The lumen 330 is further provided in communication with a slit 335 extending between the side port 332 and the distal opening 334.

In the embodiment of FIGS. 3A-3C the introducer 310 does not include an outside taper adjacent the distal end 324 of the body member 320. (Compare to outside tapers 137 and 237 of FIGS. 1A-2C.) Rather, the distal end 324 comprises a non-tapering surface that is orthogonal to the longitudinal axis of the introducer. In some embodiments an introducer may be configured without an outside taper to be used in connection with, for example, relatively larger hubs and/or elongate instruments as further detailed below.

An introducer may thus be sized to work particularly with a certain type or size of elongate instrument to be introduced into a certain type or size of hub and/or catheter. For example an introducer may be sized to work in connection with hubs or catheters of any size, including between about 2F and about 13F. Sizes much larger and much smaller than this range are likewise within the scope of this disclosure.

Figure 4:
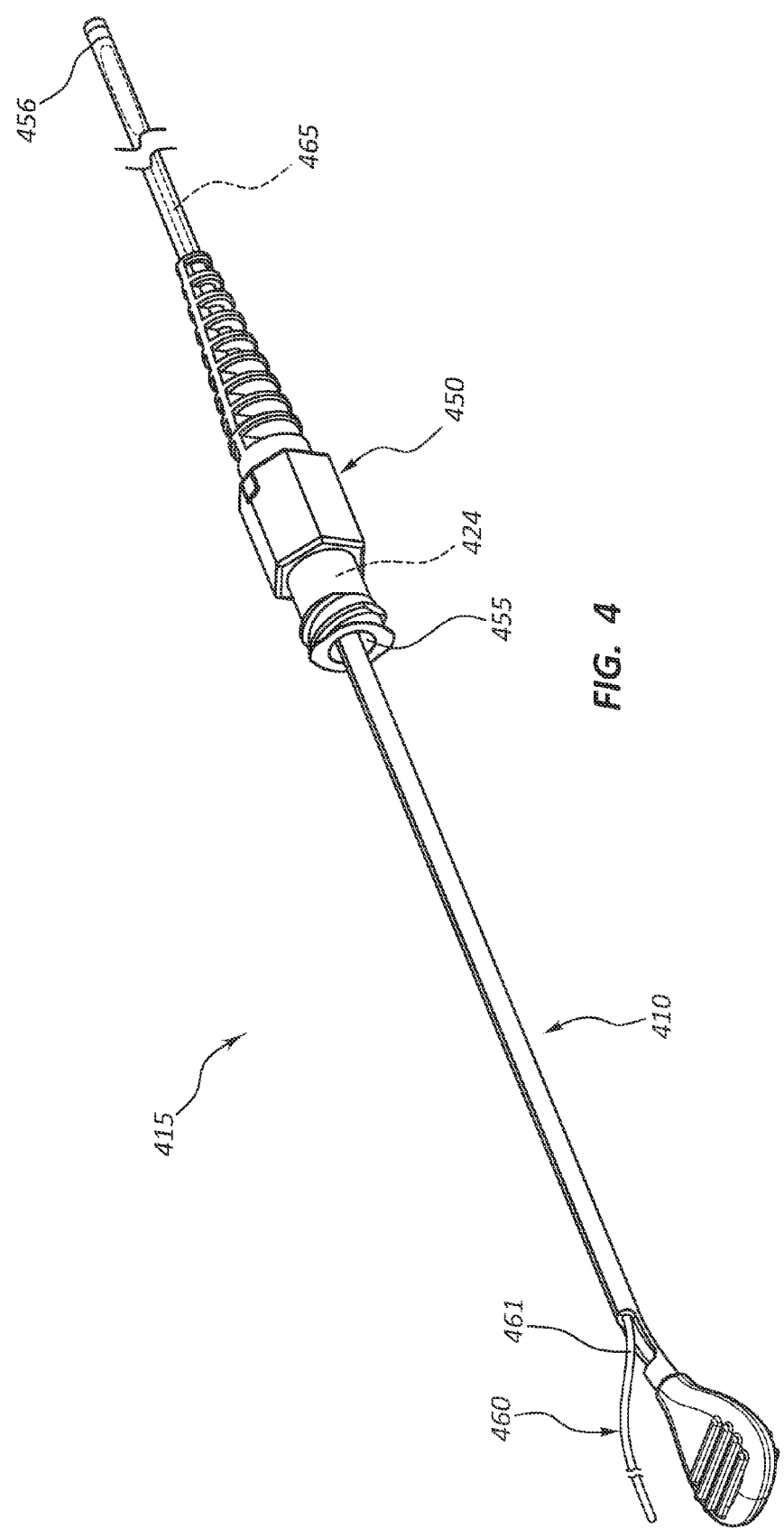
FIG. 4 is a perspective view of an introducer assembly comprising an introducer, a hub, and a snare.

FIG. 4 is a perspective view of an introducer assembly 415 comprising an introducer 410, a hub 450, and a snare 460. In the illustrated embodiment, the distal end 424 of the introducer 410 is disposed within the hub lumen 455. The snare 460 is disposed within the introducer 410 and hub 450 with a portion of the elongate body 461 of the snare 460 disposed within the introducer 410, a portion of the elongate body 461 of the snare 460 disposed within the hub lumen 455, and the snare loop 465 disposed within a catheter 456 coupled to the hub 450.

Though many of the embodiments described herein may only reference a hub, such as hub 450, it is within the scope of this disclosure for such hubs to be coupled to elongate delivery devices, such as catheters, or other tubular members. Furthermore, hubs, such as hub 450 may be configured with luer or other connectors on one or both longitudinal ends.

FIGS. 5A, 5B, and 5C are cross sectional views showing three embodiments of introducers 510a, 510b, 510c disposed within a hub 550. The hub 550 comprises a hub body 551 with a hub lumen 555 extending through the hub body 551. Thus, the hub lumen 555 may be understood as defining an inside diameter of a lumen within the hub body 551. In the illustrated embodiment, the hub lumen 555 is configured with a inside hub taper 558 which may be configured such that the diameter of the hub lumen 555 transitions from a relatively larger size to a relatively smaller size over a portion of the hub lumen 555 from the proximal end 552 of the hub body 551 to the distal end 554 of the hub body 551.

As shown in each of FIGS. 5A-5C, the inside hub taper 558 may be configured to interact with the outside diameter of a portion of an introducer 510a, 510b, 510c disposed within the hub 550. In some embodiments, the interaction of the inside hub taper 558 and the introducer 510a, 510b, 510c, may be configured to result in a frictional force that tends to hold the introducer 510a, 510b, 510c in the hub 550. In some embodiments, such as introducers 510a and 510b, an introducer may also be configured with an outside taper 537a, 537b which may mate with the hub taper 558, provide increased contact area, and increased frictional forces, in some instances. In another embodiment, such as 510c the introducer may have no such outside taper, but still be retained within the hub 550 due to friction between the introducer 510c and the hub taper 558.

This tendency for the introducer 510a, 510b, 510c to remain within the hub 550 once inserted, due to frictional forces between the hub taper 558 and the introducer 510a, 510b, 510c may facilitate one handed operation in some instances. For example, once the introducer 510a, 510b, 510c is inserted into the hub 550, it may not be necessary for a practitioner to continue to hold the introducer 510a, 510b, 510c in place due to the hub taper 558 and the resultant frictional forces. Thus, the design may enable a practitioner to have a free hand available to, for example, thread a snare 560 into the catheter 556 attached to the hub 550.

Additionally, in certain embodiments, such as 510a, an introducer may be configured with an inside taper 538a adjacent the distal end of the introducer 510a. This inside taper 538a may comprise a taper from a larger inside diameter to a smaller inside diameter of the introducer lumen 530 from a first location to a second, more distal location, along the longitudinal axis of the introducer 510a. In some embodiments, an inside taper 538a may facilitate threading a relatively small instrument, such as a snare 560, through the distal opening in the introducer 510a and into a relatively small hub 550. In other embodiments, such as 510b and 510c, the introducer may not have an inside taper.

FIGS. 6A-6F illustrate steps of one exemplary embodiment of utilizing an introducer 610 to facilitate introduction of an elongate instrument, such as a snare 660, into a sheath, such as a catheter. As with the other drawings and disclosure, this exemplary embodiment is intended to illustrate one embodiment of using an introducer. For example, alternative embodiments may not include each step described below, and/or may alter the order of operations of the exemplary embodiment.

Referring first to FIG. 6A, a snare 660 having an elongate body 661 defining a proximal end 662 and a distal end 664 has a loop 665 coupled to the distal end 664 of the elongate body 661. A practitioner may first insert the proximal end 662 of the snare 660 into the distal opening 634 of the introducer 610, as indicated by the arrows. Also as indicated by the arrows, the practitioner may then begin to feed the elongate body 661 of the snare 660 into the introducer lumen 630 toward the side port 632. In some instances the tab 640 may provide a location at which a practitioner may grasp the introducer 610 without interfering with the threading process. Further, as described above, in some embodiments a bend 645 may facilitate threading of the proximal end 662 of the snare 660 through the introducer lumen 630, because the side port 632 and distal opening 634 of the introducer 610 are aligned due to the bend 645.

FIG. 6AA illustrates another method of loading a snare 660 into an introducer 610. In the embodiment of FIG. 6AA, the snare 660 may be loaded into the introducer 610 by inserting the distal end 664 of the snare 660 into the side port 632. This method may be used, for instance, in embodiments where the snare 660 is particularly long or other instances wherein a practitioner prefers not to thread the entire snare 660 through the introducer 610. In some instances, a practitioner may compress the snare loop 665 (as indicated by the arrows) between his or her fingers while inserting the distal end 664 of the snare 660 into the side port 632. The size and shape of the side port 632 may be configured to facilitate threading of particular snares or other devices in this manner.

Figure 6B:
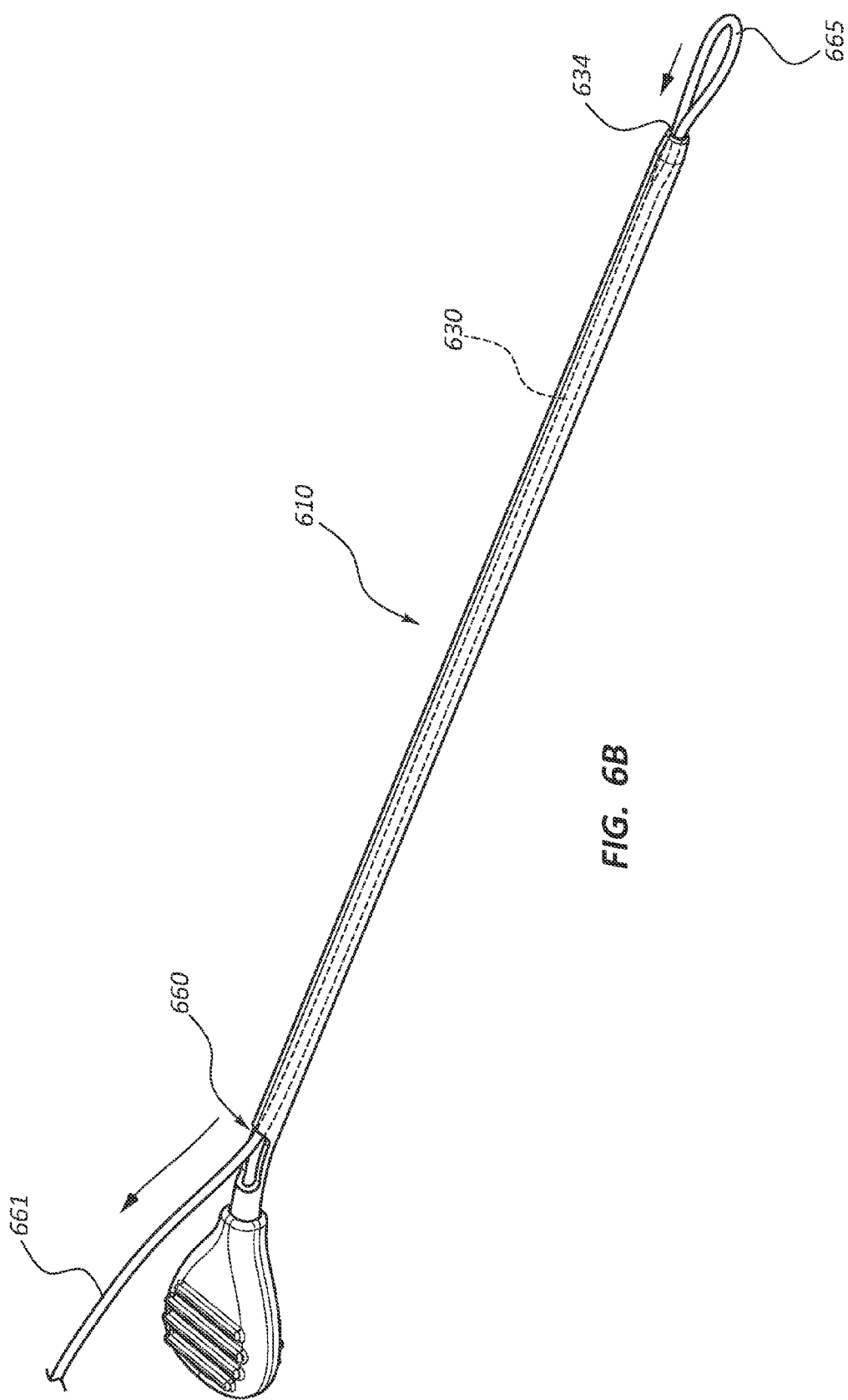
FIG. 6B is a perspective view of the introducer and snare of FIG. 6A with the snare partially drawn into the introducer.

FIG. 6B illustrates the configuration of FIG. 6A, with the snare 660 further advanced into the introducer 610. As shown in FIG. 6B, a practitioner may feed the elongate body 661 of the snare 660 into the introducer lumen 630, as indicated by the arrows, such that the loop 665 of the snare 660 begins to be drawn within the introducer lumen 630. FIG. 6B illustrates the snare loop 665 partially drawn into the introducer lumen 630. Thus drawing the snare loop 665 into the introducer lumen may tend to straighten, align, or flatten the snare loop 665 with respect to the elongate body 661 of the snare 660.

Figure 6C:
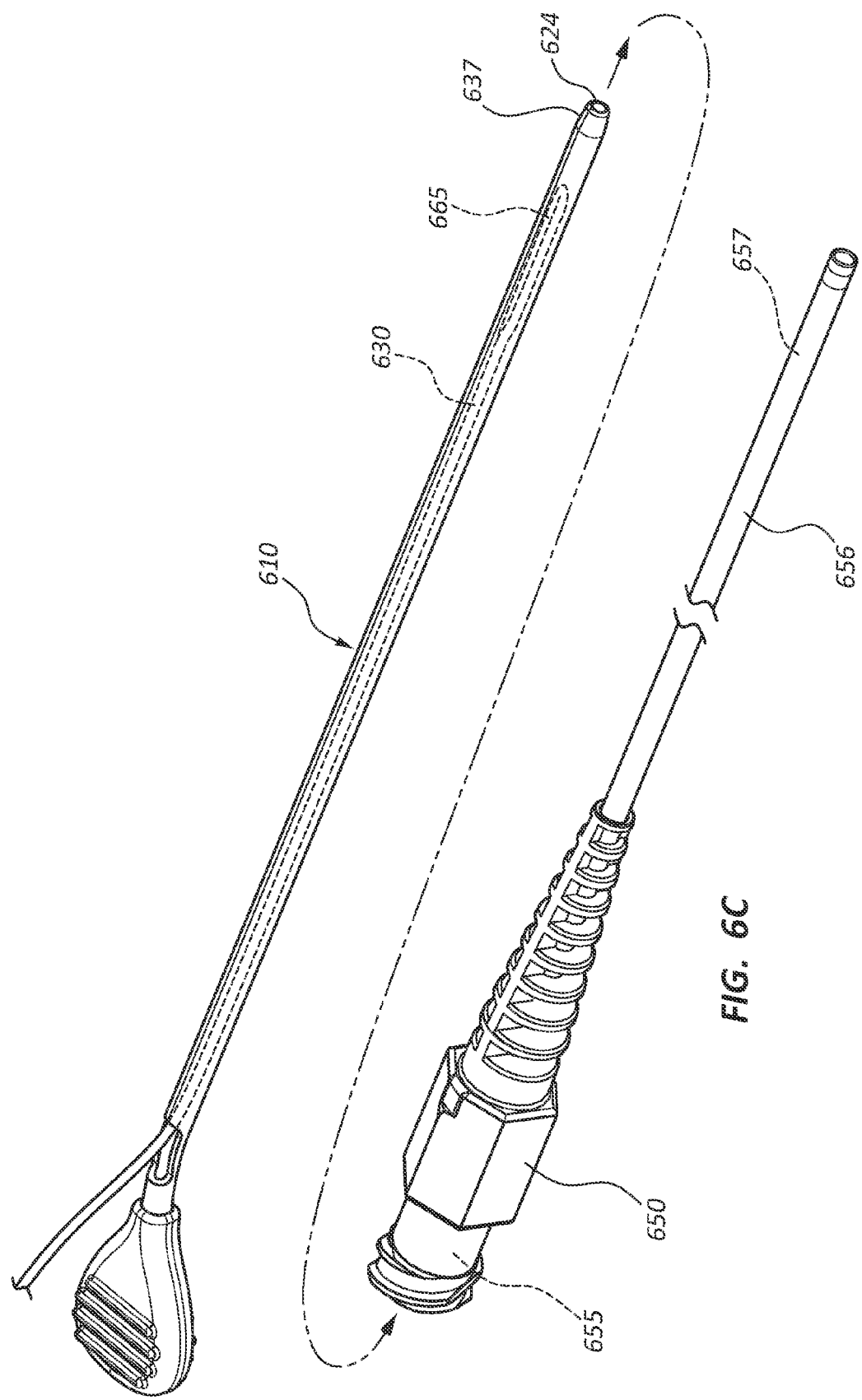
FIG. 6C is a perspective view of the introducer and snare of FIG. 6B shown with a hub and catheter.

FIG. 6C illustrates the snare loop 665 fully drawn into the introducer lumen 630. Thus withdrawn into the introducer 610 the snare loop 665 may be more easily fed into a hub lumen 655. For instance, a snare loop 665 may be difficult to insert directly into a hub lumen 655 due to the size or shape of the loop. For example, in some embodiments a snare loop 665 may be biased in an open or expanded shape, making insertion into a small lumen difficult. Similarly, other elongate instruments may be more easily fed into a hub lumen 655 through use of an introducer 610. For instance, some guidewires may have relatively flexible distal tips, use of an introducer 610 may facilitate insertion of such guidewires into hub lumens 655 as the introducer 610 may be stiffer, and thus more easily inserted, into the hub lumen. An analogous principle applies to threading any elongate instrument into a hub or lumen.

As also described above in connection with FIG. 5A-5C, a hub taper (558 in FIG. 5A-5C) may be configured to provide a frictional force, tending to hold the introducer 610 in the hub 650 once inserted. This may enable a practitioner to release the introducer 610 once inserted while completing the remaining steps of the process. In some embodiments an outside taper 637 on the introducer 610 may also be configured to contact or mate with the hub taper (558 in FIGS. 5A-5C).

As indicated by the arrow in FIG. 6C, once the snare loop 665 is partially or fully drawn into the introducer 610, the distal end 624 of the introducer 610 may then be inserted into the hub lumen 655. The hub 650 may be coupled to a catheter 656 in some embodiments, the hub lumen 655 in communication with a catheter lumen 657 disposed within the catheter 656.

Figure 6D:
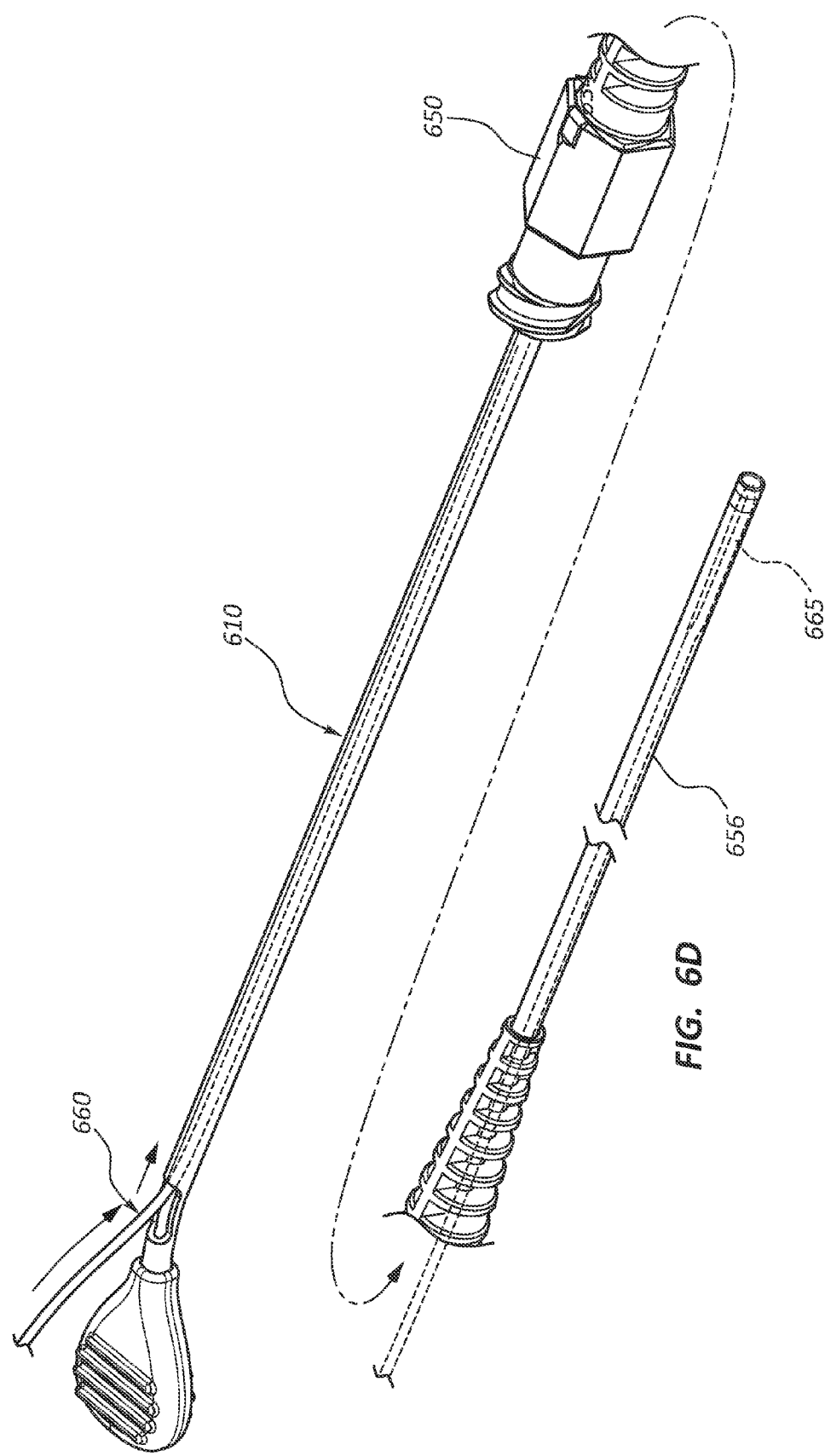
FIG. 6D is a perspective view of the introducer, snare, hub, and catheter of FIG. 6C with the introducer disposed within the hub.

FIG. 6D illustrates how the snare 660 may then be fed through the introducer 610, hub 650, and catheter 656 from a proximal position along the longitudinal axis of the introducer 610 toward a distal position. The snare 660 may be advanced within the catheter 656 until the snare loop 665 is adjacent a distal end of the catheter 656, deployed from the distal end of the catheter 656, or anywhere within the body of the catheter 656, for example.

Figure 6E:
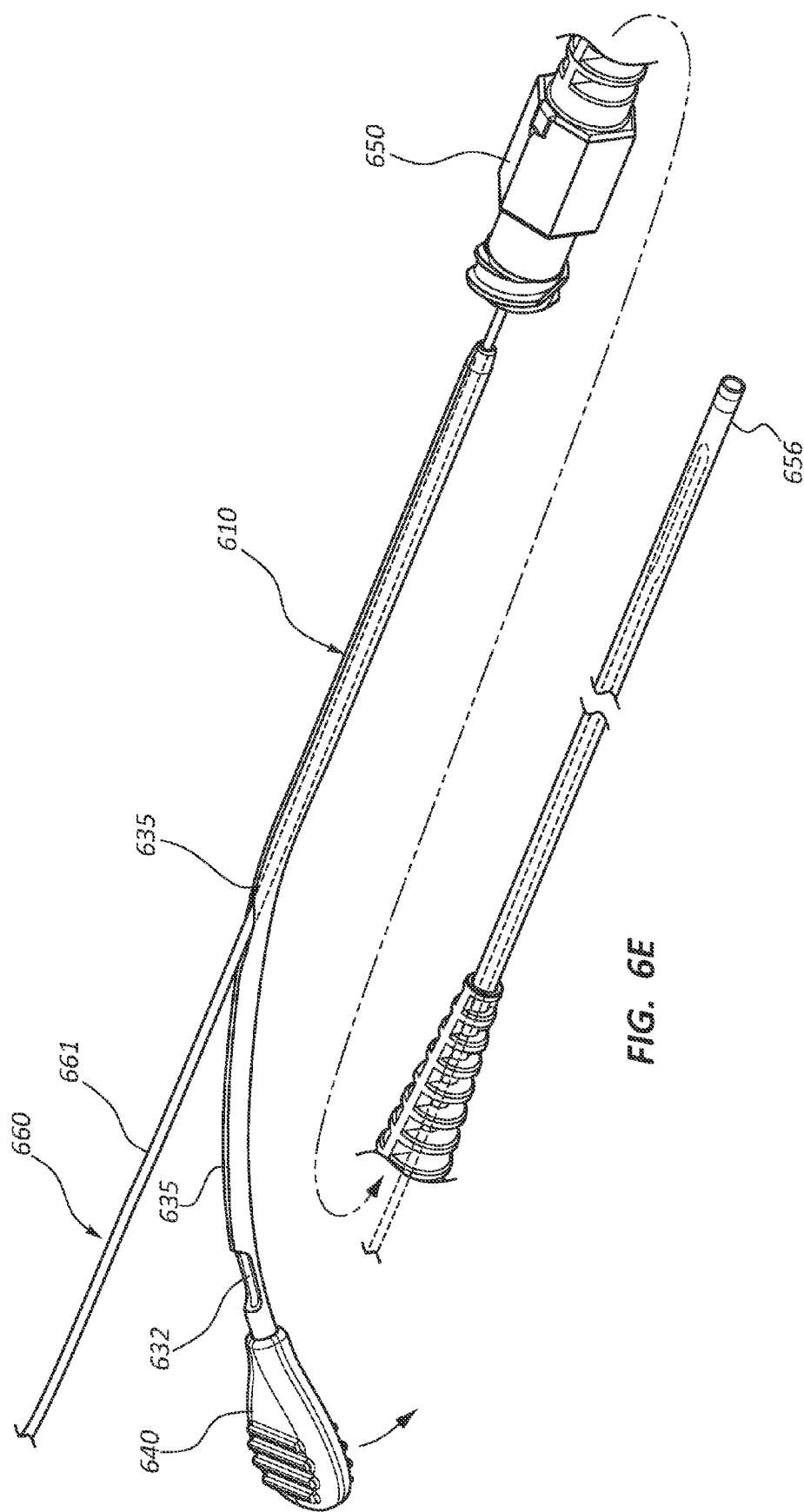
FIG. 6E is a perspective view of the introducer, snare, hub, and catheter of FIG. 6D with the introducer partially removed from the snare.

FIG. 6E illustrates how the slit 635 in the introducer 610 may enable a practitioner to remove the introducer 610 without removing the snare 660 from the hub 650 or catheter 656. As indicated by the arrows, the introducer 610 may be pulled off the elongate body 661 of the snare 660 through the slit 635, to "tear away" or remove the introducer 610. In some instances this may be accomplished by grasping the tab 640 and pulling the introducer 610 from the elongate body 661 as indicated by the arrows. In some instances, the elongate shape of the side port 632 may facilitate passage of the elongate body 661 of the snare from the side port 632 to the slit 635.

FIG. 6F illustrates the snare 660 disposed within the hub 650 and catheter 656 once the introducer (610 of FIG. 6E) is fully removed. The snare 660 and catheter 656 may then be used, for example, in any procedure requiring a snare 660 within a catheter 656.

FIG. 7A is a perspective view of another embodiment of an introducer 710. The illustrated embodiment comprises an elongate body member 720 having a proximal end 722 and a distal end 724. A lumen 730 is disposed within the body member 720 and is in communication with a distal opening 734 and a side port 732. The illustrated embodiment also comprises an outside taper 737 and a bend 745.

FIG. 7B is a cross sectional view of the introducer of FIG. 7A, taken through plane 7B-7B. As shown in FIG. 7B, the lumen 730 within the body member 720 may be configured with protrusions 770 extending inward from the inside diameter of the lumen 730. The protrusions 770 may be configured to interact with an elongate instrument inserted into the introducer 710, such that friction between the protrusions 770 and the elongate instrument tend to keep the elongate instrument from inadvertently sliding out of the introducer 710. The protrusions 710 may be configured with varied shapes and geometries, including embodiments wherein the protrusions comprise annular rings around the inside diameter of the lumen 730. In some embodiments, protrusions may facilitate use of the device as the physician need not constantly hold the elongate instrument to prevent slippage.

FIG. 7C is a cross sectional view of another embodiment of protrusions 775. In the embodiment of FIG. 7C, the protrusions are angled, such that they extend from the inside diameter of the lumen 730 in a generally proximal to distal direction. Directional protrusions, such as the protrusions 775 of FIG. 7C may be configured to prevent an elongate instrument from slipping in a particular direction. For example, the protrusions 775 of FIG. 7C may be configured to allow an elongate instrument to be advanced from the proximal direction toward the distal direction (for example in embodiments wherein the instrument is inserted through the side port) with relatively little friction, while providing a relatively greater amount of frictional resistance to translation of the elongate instrument in the opposite direction. In some embodiments directional protrusions may extend opposite those illustrated, that is, in a generally distal to proximal direction.

The examples and embodiments disclosed herein are to be construed as merely illustrative and exemplary, and not a limitation of the scope of the present disclosure in any way. It will be apparent to those having skill with the aid of the present disclosure in the art that changes may be made to the details of the above-described embodiments without departing from the underlying principles of the disclosure herein. It is intended that the scope of the invention be defined by the claims appended hereto and their equivalents.

The invention claimed is:
1. An introducer assembly comprising:
   an introducer comprising:
      an elongate introducer body member defining a proximal end, a distal end, and a bend adjacent the proximal end;
      an introducer lumen disposed within the introducer body member;
      a distal opening in the introducer body member, the distal opening positioned adjacent the distal end of the body member, the distal opening in communication with the introducer lumen; and a side port having a first width and being positioned at the bend, wherein the side port extends through a sidewall of the body member, the side port being in communication with the introducer lumen;

a slit in the sidewall of the introducer body member, the slit having a second width and extending from the distal opening to the side port, wherein the slit is in communication with the introducer lumen and wherein the second width is less than the first width;

wherein a longitudinal axis of the elongate body member comprises a distal portion that extends distally from the bend and a proximal portion that extends proximally from the bend, wherein the proximal portion of the longitudinal axis is angled relative to the distal portion of the longitudinal axis; and a hub comprising:
  a hub body defining a proximal end, a distal end, and a longitudinal axis between the proximal and distal ends; and
  a hub lumen disposed within the hub body;

wherein the hub lumen comprises a first taper configured to mate with a distal portion of the body member of the introducer in frictional engagement.

2. The introducer assembly of claim 1, wherein the distal portion of the introducer body member comprises a second taper configured to mate with the first taper of the hub lumen.

3. The introducer assembly of claim 2, wherein the introducer body member further comprises an inside taper such that a diameter of the introducer lumen at a proximal end of the inside taper is larger than a diameter of the introducer lumen at a distal end of the inside taper.

4. The introducer assembly of claim 1, further comprising a tab coupled to the proximal end of the introducer body member, the tab configured to be grasped by a user.

5. The introducer assembly of claim 4, wherein the tab is coupled to the introducer body member proximal of the side port.

6. The introducer of claim 1, further comprising a plurality of protrusions extending from an inside diameter of the introducer lumen.

7. The introducer of claim 6, wherein the protrusions are directionally oriented.

8. A method of introducing an elongate instrument into the introducer assembly of claim 1, the method comprising:
  obtaining the elongate instrument;
  inserting a proximal end of the elongate instrument into the distal opening in the introducer;
  feeding the elongate instrument through the introducer lumen such that the proximal end of the elongate instrument extends from the side port and a distal tip of the elongate instrument is disposed within the introducer lumen;
  inserting the distal end of the introducer body member into the hub lumen;
  feeding the elongate instrument through the introducer lumen such that a distal end of the elongate instrument extends into the hub lumen; and
  removing the introducer from around the elongate instrument through the slit.

9. The method of claim 8, wherein inserting the distal end of the introducer body member into the hub lumen comprises frictionally engaging the introducer in the hub lumen.

10. The method of claim 8, wherein the introducer further comprises a tab coupled to the proximal end of the introducer, and removing the introducer comprises grasping the tab and pulling the introducer from the elongate instrument through the slit.

11. The method of claim 8, wherein feeding the elongate instrument through the introducer lumen comprises extending the proximal end of the elongate instrument from the side port adjacent the bend in the introducer body member.

12. The method of claim 8, wherein a plurality of protrusions extending from an inside diameter of the introducer lumen are configured to provide frictional resistance between the introducer and the elongate instrument.

* * * * *